(12) United States Patent
Moilanen et al.

(10) Patent No.: US 7,601,120 B2
(45) Date of Patent: Oct. 13, 2009

(54) METHOD AND DEVICE FOR THE NON-INVASIVE ASSESSMENT OF BONES

(76) Inventors: Petro Moilanen, Mäkeläntie 3 as 4, FI-40900 Säynätsalo (FI); Patrick Nicholson, 29 Gensing Road, St Leonards On Sea, Sussex TN38 0HE (GB); Shu Lin Cheng, Lehtokatu 8, FI-40630 Jyväskylä (FI); Jussi Timonen, Sonidintie 5 C, FI-40630 Jyväskylä (FI)

( * ) Notice: Subject to any disclaimer, the term of this patent is extended or adjusted under 35 U.S.C. 154(b) by 869 days.

(21) Appl. No.: 10/496,559

(22) PCT Filed: Nov. 28, 2002

(86) PCT No.: PCT/FI02/00957

§ 371 (c)(1),
(2), (4) Date: May 25, 2004

(87) PCT Pub. No.: WO03/045251

PCT Pub. Date: Jun. 5, 2003

(65) Prior Publication Data

US 2005/0004457 A1    Jan. 6, 2005

(30) Foreign Application Priority Data

Nov. 30, 2001 (FI) .................... 20015044
Oct. 17, 2002 (FI) .................... 20025046

(51) Int. Cl.
*A61B 8/00* (2006.01)

(52) U.S. Cl. ............ 600/438; 600/442; 600/449; 73/599

(58) Field of Classification Search ............ 600/442, 600/437, 438, 449; 73/599
See application file for complete search history.

(56) References Cited

U.S. PATENT DOCUMENTS 3,805,596 A * 4/1974 Klahr .................... 73/602

(Continued)

FOREIGN PATENT DOCUMENTS

GB    2257253    1/1993

(Continued)

OTHER PUBLICATIONS

D. Fah and E. Stussi, "Phase velocity measurement of flexural waves in human tibia", J. Biomachanics vol. 21, No. 11, pp. 975-983, 1983.*

(Continued)

*Primary Examiner*—Eric F Winakur
*Assistant Examiner*—Katherine L Fernandez
(74) *Attorney, Agent, or Firm*—Fildes & Outland, P.C.

(57) ABSTRACT

A method for the in vivo non-invasive characterization of the material and architectural properties of a bone in which an ultrasonic wave is introduced into a bone in such way as to produce one or more guided wave modes within the bone, and the signals emerging from the bone are stored and analyzed to determine the propagation characteristics of the guided wave/s. These measured guided wave propagation characteristics are then processed to obtain estimates of desired bone properties such as cortical thickness, bone density and bone elastic constants. The invention also includes an unltrasound arrangement with movable transducers.

22 Claims, 8 Drawing Sheets

U.S. PATENT DOCUMENTS

| | | | | |
|---|---|---|---|---|
| 5,038,787 | A | * | 8/1991 | Antich et al. ............... 600/437 |
| 5,197,475 | A | | 3/1993 | Antich et al. |
| 5,259,384 | A | * | 11/1993 | Kaufman et al. ............ 600/442 |
| 5,427,106 | A | * | 6/1995 | Breimesser et al. ......... 600/447 |
| 6,322,507 | B1 | * | 11/2001 | Passi et al. .................. 600/437 |
| 6,375,617 | B1 | * | 4/2002 | Fraser ........................ 600/443 |
| 6,468,215 | B1 | * | 10/2002 | Sarvazyan et al. .......... 600/438 |

FOREIGN PATENT DOCUMENTS

| | | | | |
|---|---|---|---|---|
| GB | 2257253 | A | * | 1/1993 |

OTHER PUBLICATIONS

W. H. Prosser, M. D. Seale and B. T. Smith, "Time-frequency analysis of the dispersion of Lamb modes", J. Acoust. Soc. Am. 105(5), May 1999.*

Laugier, P. et al. "Quantitative Ultrasound for Bone Status Assessment". IEEE Ultrasonics Symposium, 2000, pp. 1341-1350, see p. 1345, col. 1.

Nicholson, P.H.F. et al. "Guided ultrasonic waves in long bones: modelling, experiment and in vivo application". Physiological Measurement, 2002, vol. 23, pp. 755-768.

* cited by examiner

Table 1. Ultrasound and bone mineral density in normals and osteoporotics

|  | Normal (n=8) | Osteoporotic (n=8) | Difference | p value |
|---|---|---|---|---|
| First wave velocity | 3946 (190) m/s | 3867 (165) m/s | -2% | ns |
| Second wave velocity | 1615 (60) m/s | 1399 (117) m/s | -15% | 0.0004 |
| Tibial SOS* | 3800 (179) m/s | 3771 (186) m/s | -1% | ns |
| Cortical BMD** | 1018 (39) mg/ml | 920 (111) mg/ml | -11% | ns |

METHOD AND DEVICE FOR THE NON-INVASIVE ASSESSMENT OF BONES

FIELD OF THE INVENTION

The invention relates to a method and a device for assessing human bones in vivo using ultrasonic waves. The invention relates to the production and detection of guided ultrasonic waves propagating within a bone, and the determination of bone properties from measured guided wave parameters.

BACKGROUND OF THE INVENTION

The so-called axial transmission technique has been used to assess long bones for over four decades (see, for example, Gerlanc et al, Clin. Orthop. Rel. Res. 1975; 111:175-180). With this method, an ultrasonic pulse is transmitted along the long axis of a bone (typically the tibia) from a transmitter to a receiver and the velocity is estimated from the transit time of the first arriving signal and the propagation distance. To account for the effects of overlying soft tissue, either a multiple transmitter/receiver configuration can be used, or transit time can be determined as a function of distance as one transducer is moved relative to the other. At least two commercial clinical devices for bone assessment using axial ultrasound transmission have been produced: the Soundscan 2000/Compact (Myriad Ultrasound Systems Ltd., Rehovot, Israel) operating at 250 kHz, and the Omnisense (Sunlight Medical Corp., Rehovot, Israel) operating at 1.25 MHz (see patent no. WO 99/45348). A recent investigation by Camus et al (J Acoust. Soc. Am. 2000; 108:3058-3065) into the axial transmission technique indicated that, under certain conditions, the first arriving signal can correspond to a lateral wave (or head wave) propagating along the surface of the solid at the bulk longitudinal velocity. The conditions under which lateral waves were observed included an appropriate measurement geometry (in terms of the separation of the transducers and their distance from the surface), an approximately point-like transmitter and receiver (spherical wavefronts), and the use of wavelengths less than the thickness of the solid layer. Tibial ultrasound velocity values measured in vivo are comparable to, or slightly lower than, in vitro measurements of the axial longitudinal wave velocity in excised human cortical bone specimens. However, there is experimental evidence indicating that the velocity of the first arriving signal is lower than the longitudinal velocity when the wavelength is greater than the bone thickness. Simulation studies show similar trends, and indicate that the waves contributing to the first arriving signal change as the sample becomes thinner. Clinical evidence for such thickness effects is, as yet, inconclusive, but this may be due to differences in the ultrasonic frequencies used by the different commercial systems, or other methodological factors.

Tibial ultrasound velocity measured using current commercial devices correlates with tibial bone mineral density (BMD), and, to a lesser extent with BMD at other skeletal sites (see, for example, Foldes et al. Bone 1995; 17:363-367), and also reflects cortical bone elastic modulus. However, tibial ultrasound is a poor discriminant of osteoporotic fracture, and is only weakly correlated with femoral strength and BMD. There are a number of reasons why current tibial ultrasound measurements may be sub-optimal in terms of their sensitivity to relevant bone properties. Waves propagating at the bone surface may preferentially reflect the material properties of bone in the periosteal region. In osteoporosis, cortical bone changes occur primarily in the endosteal region. The porosity of endosteal bone increases leading eventually to endosteal resorption, "trabecularisation", and thinning of the cortex. In addition, recent nanoindentation studies suggest there may be differential changes with aging in the elastic properties of periosteal and endosteal bone purely at the material level. Ultrasonic methods that target these known pathological changes are likely to prove more valuable clinically. A further concern is that if density and elasticity both exhibit a parallel change, for example as a result of a change in porosity, ultrasound velocity may not be altered because the two effects tend to cancel out (since longitudinal velocity varies as the square root of elasticity divided by density). These considerations suggest that any improved ultrasonic method for cortical bone assessment should be sensitive to one of more of the following factors: a) reduced cortical thickness, b) structural changes in the endosteal region, such as increased porosity, and c) changes in bone density and elasticity at the material level, ideally independently of each other.

In general, little consideration has been given to the possibility of using different types of ultrasonic waves in long bones. One exception has been work reporting low frequency ultrasonic measurements of "surface wave" velocity in the tibia, mapping the spatial variation in velocity (Jansons et al. Biomaterials 1984; 5:221-226). However, since pure surface waves only exist in structures that are much thicker than the wavelength, it is likely that these researchers were actually measuring a guided wave mode reflecting both bone thickness and material properties. Guided waves propagate within bounded or layered media, and their characteristics are determined by the geometrical and material properties of the structure and of the surrounding media They arise from the reflection, mode conversion and interference of longitudinal and shear waves within the structure (Victorov L. A. Rayleigh and Lamb Waves. New York, Plenum, 1967). Ultrasonic guided waves are quite widely used in engineering non-destructive testing for the assessment of plates, tubes and more complex structures.

SUMMARY OF THE INVENTION

The main object of the present invention is to provide a method capable of measuring the velocity of at least two ultrasonic waves propagating in a bone at the same time, where at least one of said waves is a guided wave according to Lamb wave theory. This object is achieved through a method and the device as defined in the accompanying claims. The invention makes use of the well known Lamb wave theory for guided waves in solid elastic plates, demonstrating for the first time how these guided waves can be applied for the non-invasive assessment of bones.

The cortex of human long bones essentially comprises a curved plate of solid bone, and should be capable of supporting the propagation of guided waves similar to Lamb waves. Lamb waves are two-dimensional elastic waves that propagate in a free solid elastic plate of finite thickness in a vacuum. They arise from the multiple reflection and mode conversion of longitudinal and shear waves from the upper and lower surfaces of the plate. They exist in the form of resonant modes where the combination of frequency and phase velocity corresponds to standing waves in the thickness direction. For symmetric modes, identified as S0, S1, S2, etc., the motion is symmetric about the mid-plane of the plate, whereas in anti-symmetric modes (A0, A1, A2, etc.) the motion is antisymmetric. The behavior of each mode is described by a dispersion curve which characterises the variation in phase velocity with frequency. All but the two fundamental modes, S0 and A0, have a cut-off frequency thickness product (F.d). Thus for very low frequencies, or for very thin plates, only the fundamental (S0 and A0) modes can be excited. In these conditions, the phase velocity of the S0 wave approaches that predicted by 'thin plate' theory, given by an equation analogous to the bar wave equation (Graff K. F. Wave Motion in Elastic Solids. New York, Dover, 1991). With increasing F.d, the velocities of all of the Lamb modes asymptotically approach the Rayleigh wave velocity. Lamb wave terminology is often also used to describe wave propagation in plates loaded by an external medium such as a fluid. The boundary conditions are modified by the presence of a surrounding medium and the characteristics of Lamb waves in a fluid immersed plate are different from those of Lamb waves in a free plate. For example, if the phase velocity of the fluid is close to the phase velocity of a Lamb mode, the mode continuously radiates into the fluid and therefore its attenuation is high. In this document, the term "Lamb wave" is used in its general sense to apply to guided waves propagating in plates, tubes and other geometries where there exists a solid layer, and also to cases where the solid layer is bounded by a surrounding fluid medium.

Another object of the present invention is to provide a method for exciting ultrasonic waves in a bone using low frequency small diameter contact transducers so as to preferentially produce guided waves in the bone. By measuring at low frequencies, the velocity of the first arriving wave has enhanced thickness-dependence, with a velocity tending towards that of the fundamental symmetric Lamb wave. In effect, the first arriving signal can be considered to be a guided wave in these circumstances. Low frequency small diameter transducers behave as approximately point-like transmitters and receivers, radiating energy in all directions, and coupling into additional guided waves that arrive after the first arriving signal.

Yet another object of the present invention is to provide a method for maintaining a near constant contact force between the ultrasound transducer and the limb. During in vivo measurements some movement of the patient is to be expected and this may lead to variations in contact force unless corrected for. Variations in contact force may have an adverse effect on the coupling of acoustic energy into the bone and may lead to errors in the measurements.

Further object of the present invention is to provide a method for analysing the data from an axial transmission scan in the form of an (r,t) or (distance, time) diagram, from which different propagating waves can be identified and their velocities determined from the slope of lines fitted to the waves. By using this approach, waves arriving after the first (fastest) signal can be detected and measured.

Further object of the present invention is to provide a method for enhancing the discrimination and measurement of guided waves through the use of spectral analysis applied to the received signals. This includes calculating the frequency spectrum of the received signal, calculating the spectrogram (time-frequency analysis), and performing two dimensional Fourier transform on the (r,t) data array (frequency-wavenumber analysis). Additionally, or alternatively, the received signals may be filtered to enhance or reduce specific frequency components. Additionally, or alternatively, the excitation signal sent to the transmitting transducer may be a specified arbitrary function chosen in the knowledge of the transducer frequency response so as to produce an output signal with particular characteristics.

Further object of the present invention is to provide a method for employing an array of transducers so that scanning of the receiver can be performed electronically by using different transducer elements, or combinations thereof, as receivers. In this way, the received signal can be measured as function of transmitter-to-receiver distance, and an (r,t) diagram formed as described earlier, but with the advantage that no moving parts are involved.

Further object of the present invention is to provide a method for employing a comb transducer consisting of a set of transducer elements with constant spacing between the elements. Either transmitter, receiver or both may be a comb transducer. The comb transducer excites (or detects) guided waves with a constant wavelength determined by the spacing of the elements. By chosing appropriate frequencies, selected guided waves can be produced and measured in the bone.

Further object of the present invention is to provide a method for coupling energy from ultrasound transducers into guided waves in the bone by use of transducers placed at an angle to the bone and coupled to the limb through a fluid or solid medium. Using such a method guided waves with known phase velocity may be preferentially produced, this phase velocity being determined by the angle and the velocity in the coupling medium, through Snell's law. The transducers may be in contact with the bone with a small amount of gel used to maintain acoustic coupling, or the transducers may be some distance above the limb with the acoustic signal consequently travelling some appreciable distance through the coupling medium.

In one embodiment of the invention two transducers are used in a reflection configuration at a specified angle of incidence for the transmitter (and the same angle of reflection for the receiver) to excite and detect guided waves at a single point on a bone. Minima in the reflected frequency spectra correspond to energy being coupled into guided waves in the bone. The angle of incidence/reflection may be varied to obtain data over a range of angles. The angle can be related to phase velocity through Snell's law, and hence dispersion curves may be determined. The method may be implemented using either broadband pulses, tonebursts or continuous waves. By rotating the transmitter/receiver about an axis normal to the bone surface, the anisotropy in the plane of the bone layer may be assessed.

In another embodiment of the invention, a single transducer is pulsed and used both as transmitter and receiver. Thus, the transducer is aligned at right angles to the bone surface and is operated in pulse-echo mode. The signals reflected from the bone are obtained at normal incidence. The time difference between the reflection from the upper and lower bone surfaces is used to estimate bone thickness. This time difference may be determined in the time domain. Alternatively the time difference may be determined in the frequency domain, since the frequency spectrum of the composite received signal will be modulated with a period of $dF=1/t$, where t is the time delay between the two reflected signals. The estimated thickness may be calculated as $d=v(t/2)$ where v is the sound speed in bone in the radial direction, which may be taken from the literature (typically 3300 m/s).

In another embodiment of the invention, measured guided wave acoustic parameters, such as the velocities of different guided wave modes and/or the velocity of specific modes at different frequencies, are used as input data to a mathematical inversion algorithm. The outputs from this algorithm are estimates of bone properties of interest, potentially including bone thickness, bone density, bone elastic constants (elastic modulus, Poisson ratio). The mathematical inversion algorithm is based on an iterative process using analytical guided wave theory. Initial estimates of the bone properties are used to calculate guided wave acoustic parameters from guided wave theory. These are compared with the measured acoustic parameters, and then the initial estimates of bone properties are adjusted in such a way as to reduce the overall error, and the process is repeated until the error becomes acceptably small. Additionally or alternatively, an artifical neural network may be used to obtain estimates of bone properties from the measured acoustic parameters. Additionally, or alternatively, an estimate of the bone thickness obtained using said forementioned reflection measurement may used as an additional input to the mathematical inversion algorithm.

Further object of the present invention is to provide a method for detecting and localising regions with abnormal bone properties. To achieve this guided wave measurements may be made at a number of locations in the bone so that regions with abnormal properties may be detected. One application would to detect the presense of so-called stress fractures within the bone. Stress fractures are often very difficult to observe on x-ray images because of their small size, but they will have a large effect on Lamb wave propagation through the bone. In addition, measurements may be made at a region of particular interest, for example, at the site of a healing fracture, in order to monitor changes in bone properties.

These and other features and advantages of the invention will be more fully understood from the following detailed description of the invention taken together with the accompanying drawings.

DETAILED DESCRIPTION OF THE INVENTION

Figure 1:
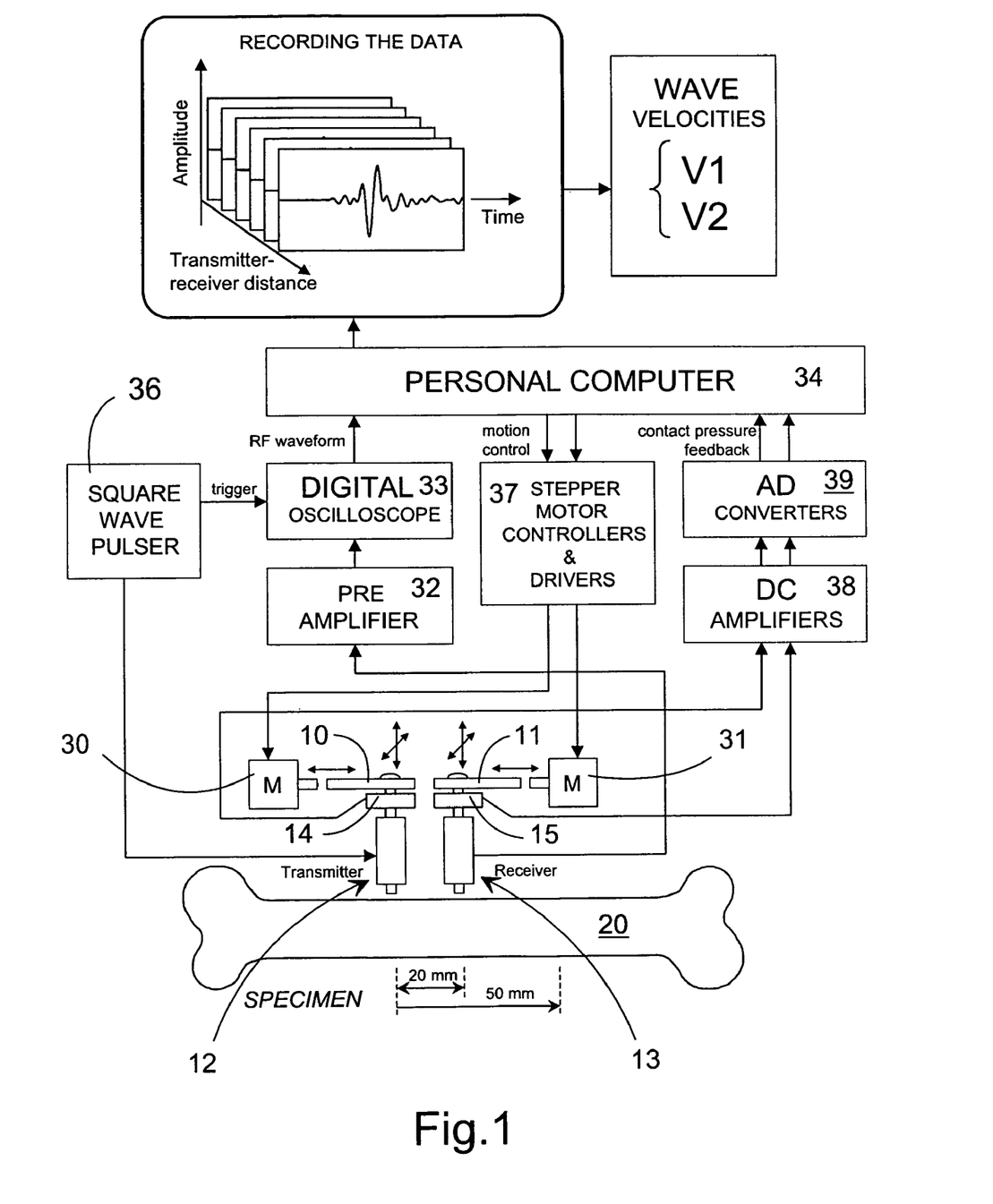
FIG. 1. Schematic diagram of the axial transmission measurement system for a preferred embodiment of the invention.

FIG. 1 illustrates the measurement system of the first embodiment of the invention. A pair of non-focused contact transducers 12, 13 with a center frequency of approximately 200 kHz and a diameter of 6 mm are used. The transducers are orientated perpendicularly to the surface of the object 20 to be measured and a coupling medium, which may be ultrasonic gel, a soft plastic, or some other fluid or solid medium or media is applied. The transmitter is kept at a fixed axial position during the measurement, but the receiver is moved progressively under computer control 34, 37, with the transmitter-receiver distance increased typically from $r_0$=20 mm to r=50 mm by 0.5 mm steps. The main movement axis is automated by a stepper motor 30, 31 controlled linear actuator with a maximum line accuracy of 0.015 mm (RK Rose+ Krieger trapezoid linear unit 303300 30 driven by bipolar Superior Electric stepping motor, model KLM091F13 with stepping module 430-T). Transducer contact pressures are determined by the load cells 14, 15 (Sensotec Inc, model 31). The DC readings are amplified and A-D converted (National Instruments 7344) 38, 39. The transmitting transducer is excited by a square wave pulser 36 (Panametrics 5077PR) with an amplitude variable from 100 V to 400 V. Signals from the receiver are amplified with a custom-made charge amplifier 32 with 40 dB voltage gain and are then acquired by a digital oscilloscope 33 (National Instruments 5102) with sampling rate of 10 MSPS. The data acquisition is trigged by the pulser at a pulse repetition frequency (PRF) of 200 Hz. Software for data acquisition and analysis is implememented using LabView (National Instruments) with Matlab also used for some analyses.

Figure 2:
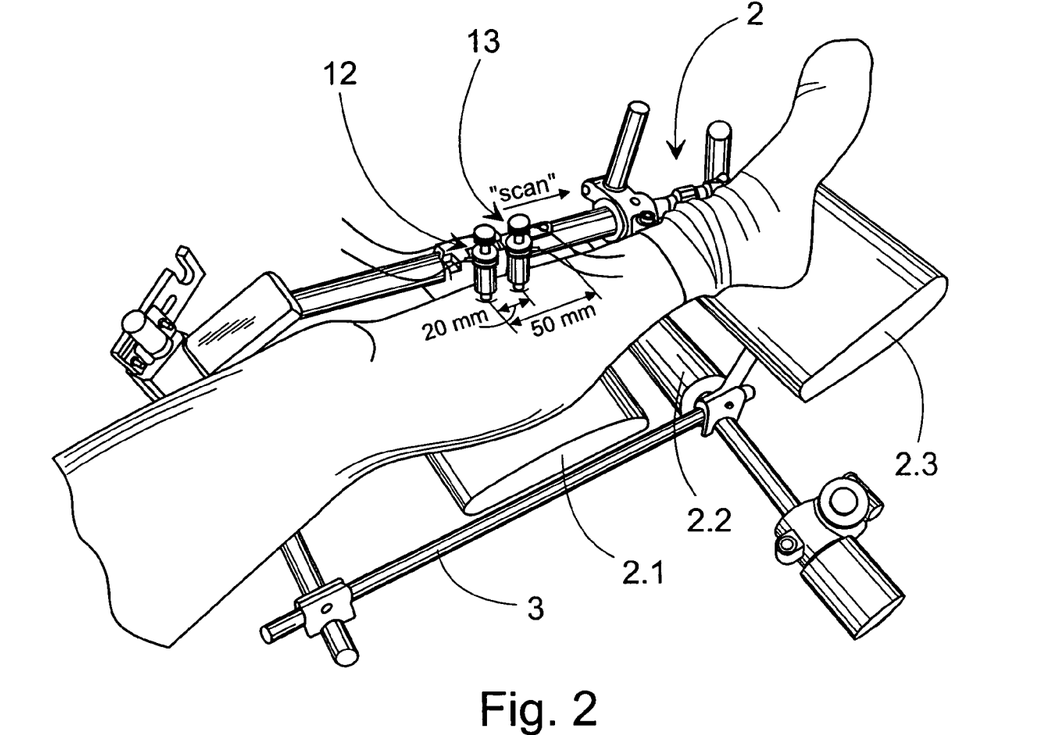
FIG. 2. Leg support on the chair and transducers in contact with the patient's leg.

FIG. 2 shows the leg support on the chair. The first embodiment of the invention includes a chair (not shown) with an attached leg support 2 and a ultrasound scanning device mounted on the leg support 2. The scanning device has two transducers 12, 13 (transmitter and receiver), where one transducer is fixed during the measurement and one moves along the axis of the limb being measured, and means for adjusting the position of the moving transducer automatically, and means for adjusting the vertical position of the transducers relative to the limb surface using actuators so as to achieve a specified contact force, and means for detecting the forces in the tip of each transducer (contact pressures), and means for acquiring the received signals as function of transducer separation, producing an (r,t) diagram from input data and analysing it in order to calculate the wave speeds, and, optionally, other acoustic parameters such as attenuation. In FIG. 2 transducers 12, 13 are shown separately without a supporting slide mechanism, which is further supported by the chair 1. The leg support comprises the pillows 2.1, 2.2 and 2.3 and the frame 3 supporting them and a slide mechanism of the transducers.

Alternatively both transducers can be moved, or a fixed transmitter may be used with at least two receivers which may move, or a fixed array of transducers may be used each of which may function as both transmitters and receivers.

Or fixed transmitter and at least two receivers, or fixed transducer array, or movement (scan or array) around the leg in order to detect one wave with low velocity (lower than the velocity of sound of longitudinal waves in bone).

Figure 3:
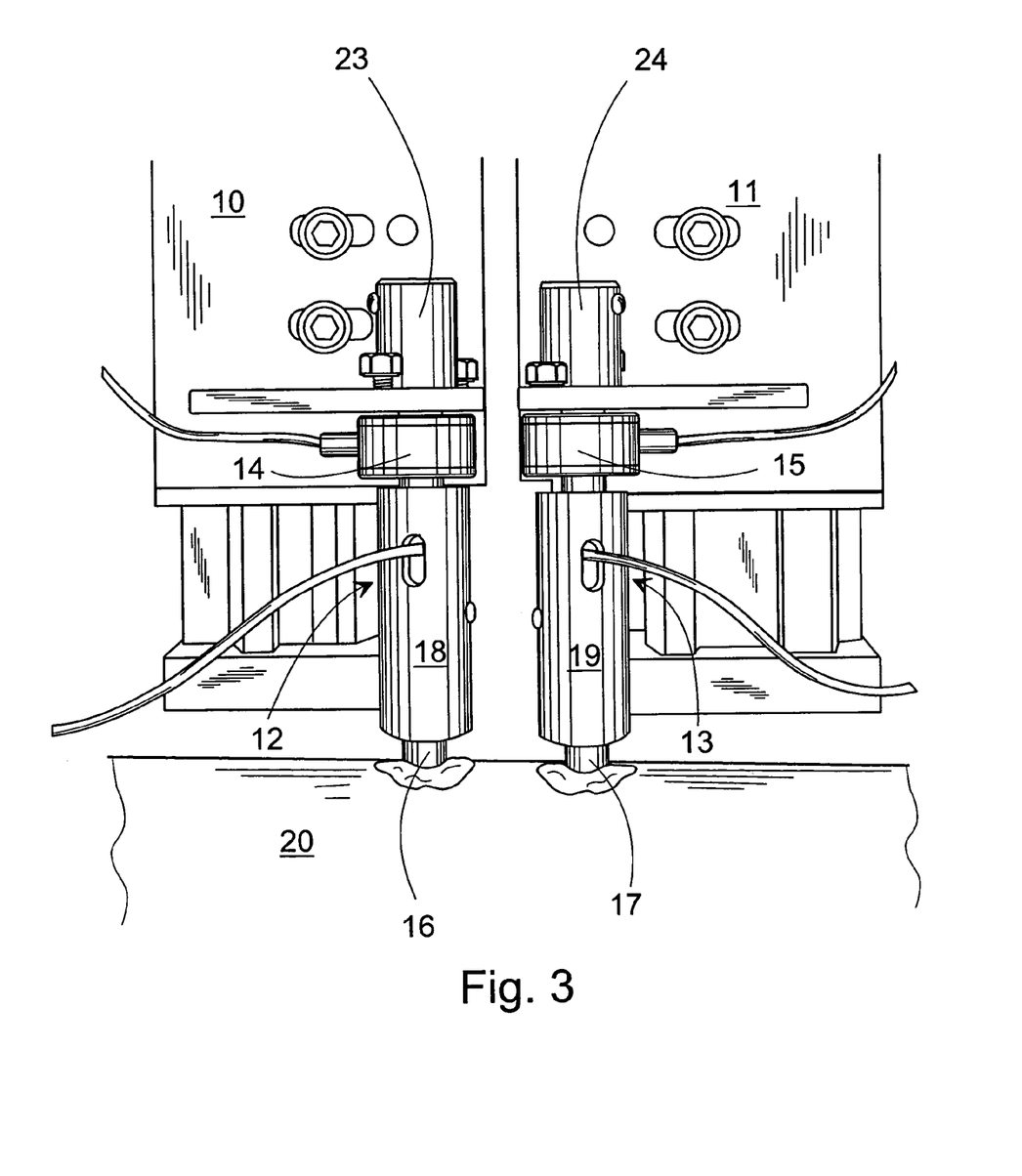
FIG. 3. Transducer units seen in front

FIG. 3 shows the transducer units seen from the front and in contact with a tibia. Each transducer 12, 13 is carried by a slide 10, 11. The transducer unit includes a transducer holder 18, 19 a force sensor 14, 15 and nuts 23, 24, which secure the transducers to the slides 10, 11. Both slides have manual positioners (not shown) for the vertical adjustment along the vertical guides 10.1, 11.1. Each one is secured to another slide moving along a horizontal guide by a stepping motor (not shown).

Figure 4:
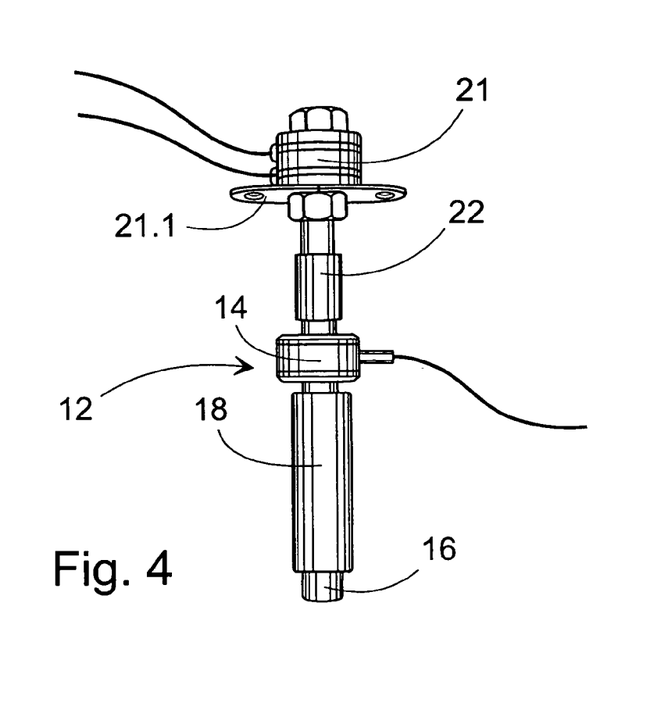
FIG. 4. Preferred transducer unit with an actuator.

FIG. 4 shows an advanced transducer unit. The unit includes a transducer holder 18, a force sensor 14 (a precision miniature load cells, Sensotec Inc, model 31), a connection sleeve and an actuator 21 (H.S.I. miniature linear actuators model 20561-05 with a stroke of 12.7 mm). The actuator allows the transducer position to be altered to maintain a specified contact force with the limb. The unit is secured to a slide by the lugs 21.1.

Figure 5A:
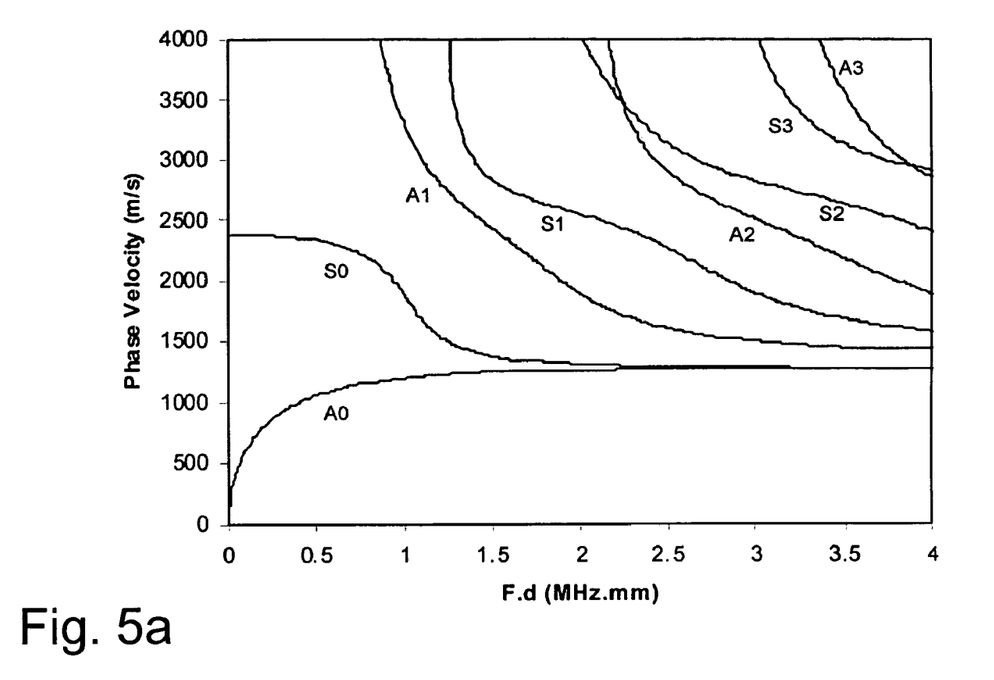
FIG. 5a. Phase velocity of guided modes, theoretical Lamb wave dispersion curves in acrylic plates.
Figure 5B:
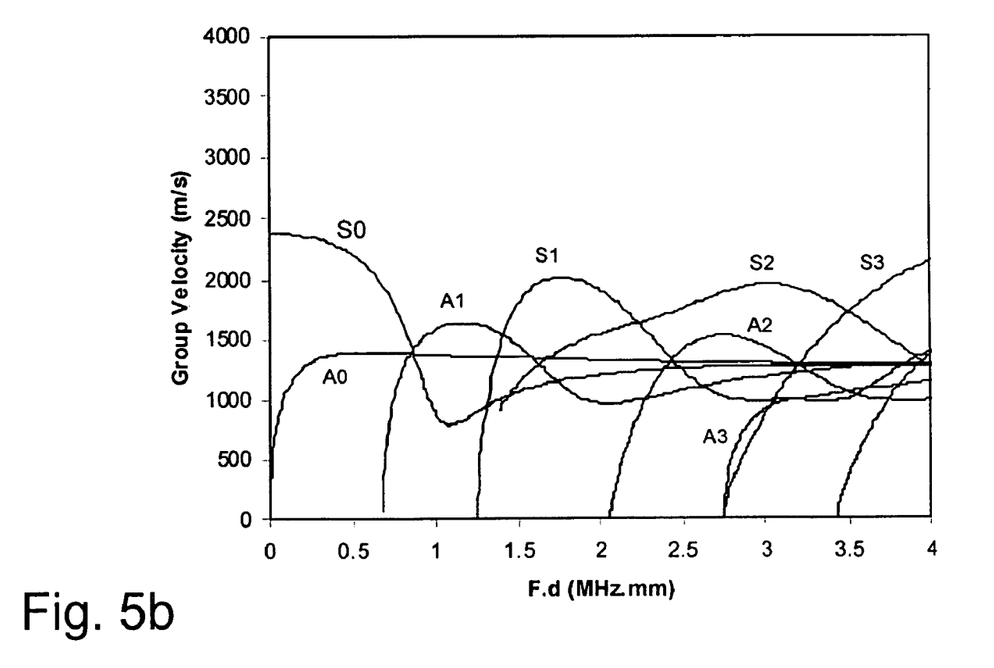
FIG. 5b. Group velocity of guided modes, theoretical Lamb wave dispersion curves in acrylic plates.

FIGS. 5a and 5b show theoretical Lamb wave dispersion curves for the first four symmetrical (S0-S3) and antisymmetrical (A0-A3), guided modes in acrylic plates: FIG. 5a) phase velocity, FIG. 5b) group velocity. The horizontal axis is the frequency thickness (F.d) product. These curves were calculated using the Rayleigh-Lamb equation assuming a longitudinal velocity of 2750 m/s and a shear velocity of 1375 m/s for acrylic. Lamb waves are two-dimensional elastic waves that propagate in a free solid elastic plate of finite thickness in a vacuum. They arise from the multiple reflection and mode conversion of longitudinal and shear waves from the upper and lower surfaces of the plate. They exist in the form of resonant modes where the combination of frequency and phase velocity corresponds to standing waves in the thickness direction. Each continuous curve in FIGS. 5a and 5b represents a guided wave mode. From these dispersion-curves it can be seen that all but the two fundamental modes, S0 and A0, have a cut-off frequency thickness product. Thus for very low frequencies, or for very thin plates, only the fundamental (S0 and A0) modes can be excited. In these conditions, the phase velocity of the S0 wave approaches that predicted by 'thin plate' theory, given by an equation analogous to the bar wave equation. At high F.d values the velocities tend asymptotically toward the Rayleigh velocity. Lamb wave terminology is often used to describe wave propagation in plates loaded by an external medium such as a fluid. The boundary conditions are modified by the presence of a surrounding medium and the characteristics of Lamb waves in a fluid immersed plate are different from those of Lamb waves in a free plate. For example, if the phase velocity of the fluid is close to the phase velocity of a Lamb mode, the mode continuously radiates into the fluid and therefore its attenuation is high.

Figure 6:
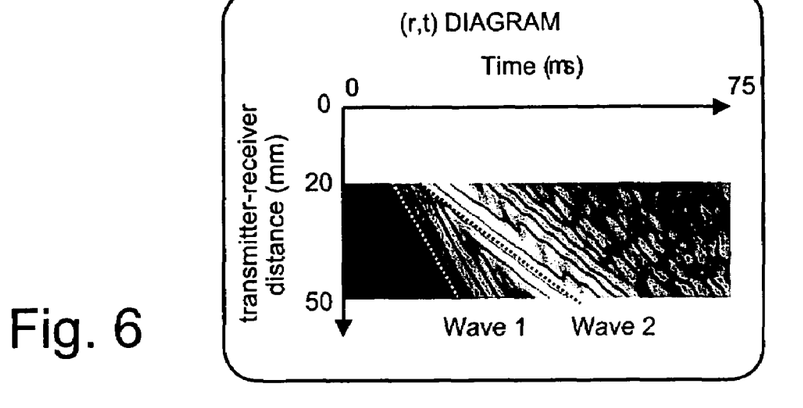
FIG. 6. An (r,t) diagram for a 3 mm thick acrylic plate.

FIG. 6 shows a so-called (r,t) diagram arising from a measurement made on a 3mm thick acrylic plate. The (r,t) diagram is produced by plotting the received radio frequency (RF) signals as a function of distance r, giving a (r,t) diagram. Each received RF waveform was plotted as a horizontal line in which absolute amplitude is mapped to a grey scale value, with the maximum amplitude corresponding to white. These horizontal lines are stacked vertically to give a so-called (r,t) diagram in which the horizontal axis was time (t) and the vertical axis was distance (r). From the (r,t) diagrams propagating wavers are visualised, and, by fitting a line to the peaks within a wave packet, velocities are measured. Two waves are observed consistently in the (r,t) diagrams shown and, because of their different characteristics, different methods are adopted to determine the velocity of each. The first arriving signal (Wave 1) is generally of a low amplitude and relatively non-dispersive, and is tracked by using a thresholding approach set at 25% of the first peak maximum. This value is selected empirically to prevent the tracking failing due to noise. Tracking of the slower wave packet (Wave 2) is more difficult due to interference from other components in the received signals. A semi-automatic approach is adopted in which the user selects a peak in the first RF line within the slower wavepacket from which to begin tracking. The software then searches forward in the next RF line using a relatively small time window to minimise the chance of jumping to another, incorrect, peak. This process continues through all of the RF lines, and then a straight line is fitted to the points. Errors can be corrected manually by the user and a new fit made. The phase velocities of the first and second waves are then calculated as the slopes of the linear fits to the points in the first and second wavepackets respectively.

Figure 7:
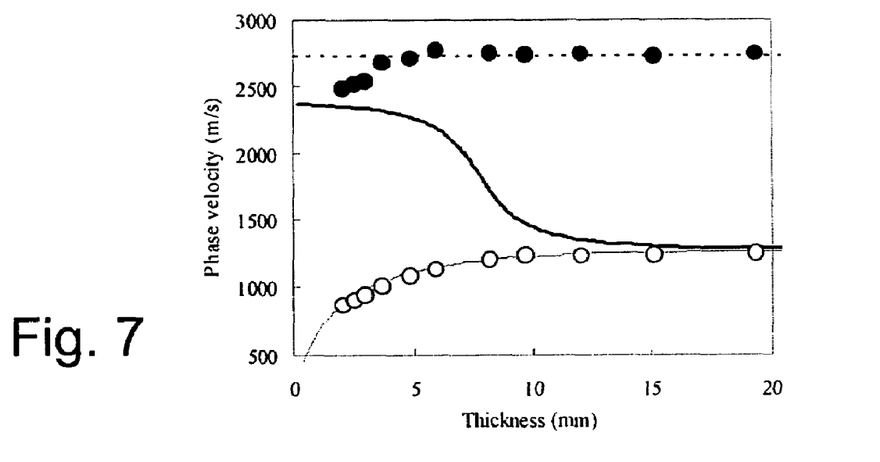
FIG. 7. Experimental and predicted data for acrylic plates.

FIG. 7 shows the results of a series of measurements on acrylic plates. The theoretical predictions for the velocity of the fundamental symmetric (S0) and antisymmetric (A0) Lamb waves are also shown. The first arriving wave (Wave 1) propagated at the longitudinal velocity in thick plates, but in thin plates velocity decreased towards that predicted for the S0 Lamb wave. Hence, in thin layers measured at low frequencies, the first arriving wave can also be cosidered to be a guided wave. The slower wave (Wave 2) agreed closely with predictions for the Lamb A0 wave, leading to the conclusion that the second wave is indeed a Lamb A0 guided wave.

Figure 8:
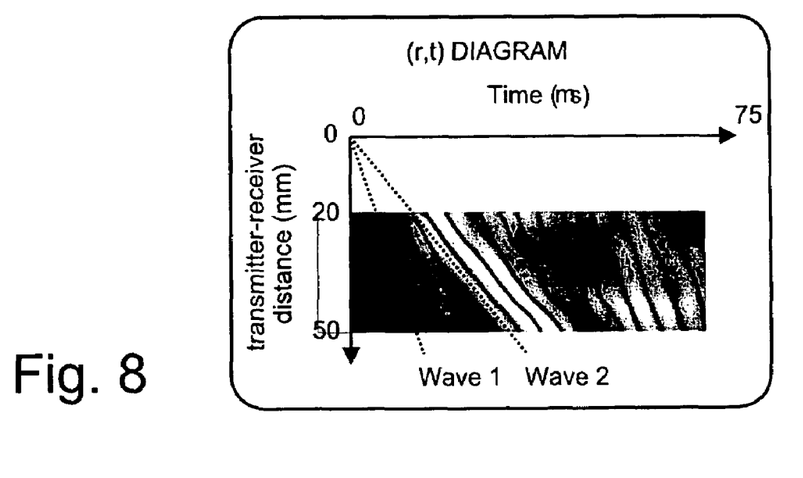
FIG. 8. An (r,t) diagram for a human tibia measured in vivo.

FIG. 8 shows an (r,t) digram obtained from measurements on a human tibia in vivo in a normal healthy volunteer. Two distinct propagating waves are again observed as in the acrylic plates.

Figure 9:
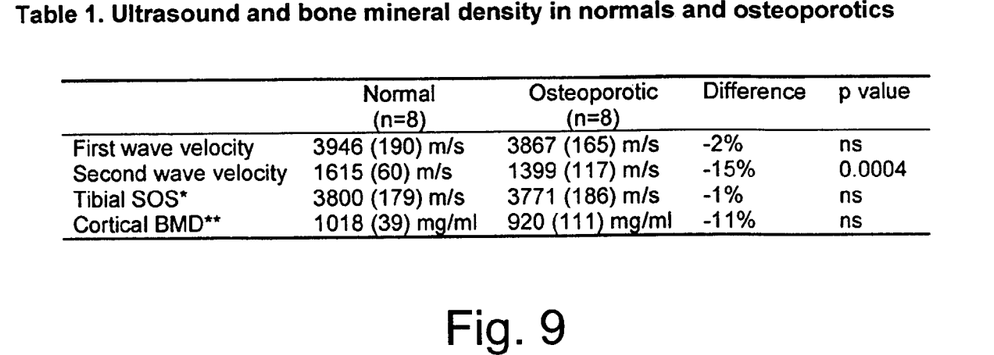
FIG. 9. Table showing ultrasound and bone mineral density results in normals and osteoporotics.

FIG. 9 is a table of results of a pilot study in which ultrasound measurements were made in normal and osteoporotic subjects. Comparing the values in the healthy and osteoporotic subjects, significant differences were found only for the slower guided wave. In osteoporotics the velocity of the slower guided wave (Wave 2) was 15% lower than in normals. These results suggest that the velocity of the A0 guided wave (i.e. the second wave) is the best discriminant of osteoporosis.

Figure 10A:
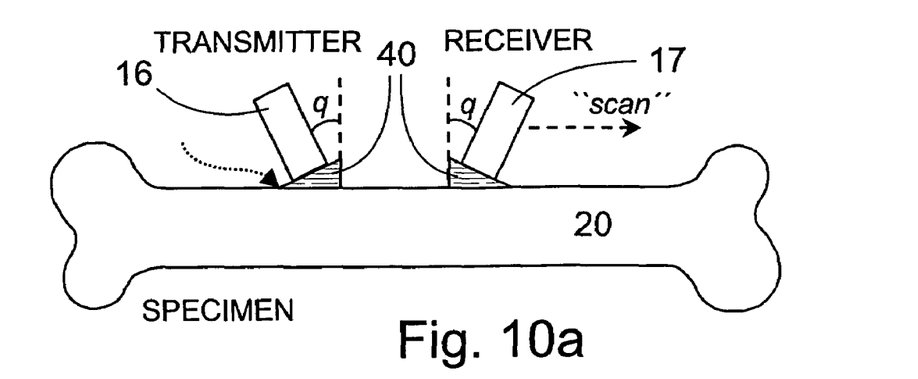
FIG. 10a-c. Alternative transducer configurations for other embodiments of the device.
Figure 10B:
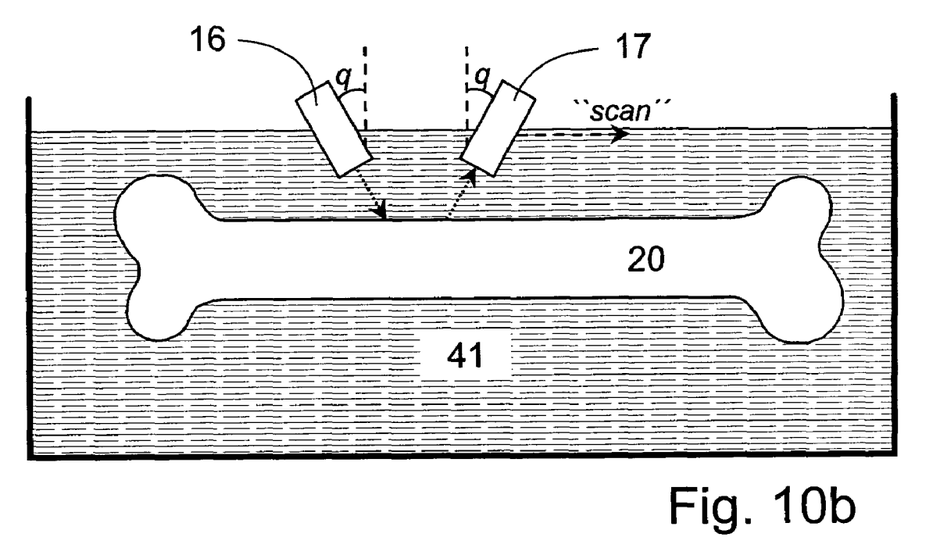
Figure 10C:
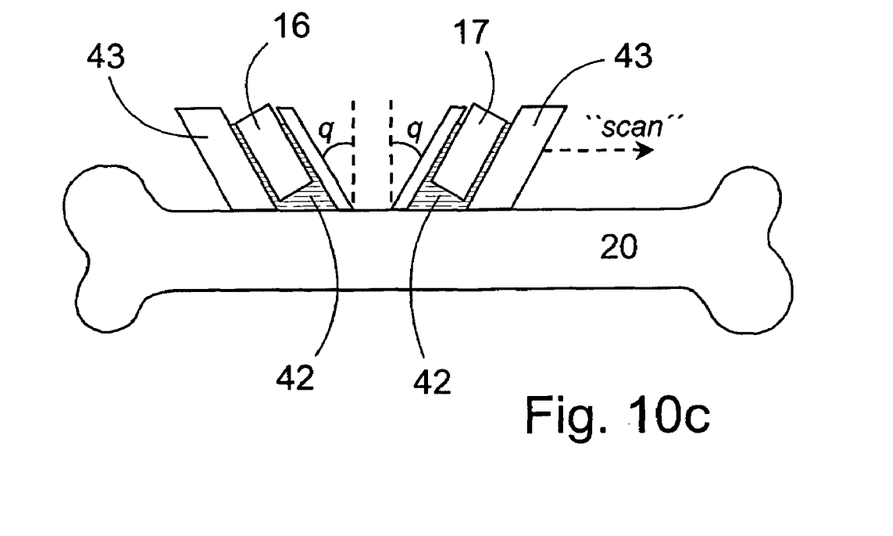

FIGS. 10a, 10b and 10c show alternative transducer configurations. The transducers 16, 17 may be coupled directly to the skin at normal incidence using gel 40, 42 (or liquid 41 in FIG. 10b) to assist coupling. Alternatively they may be placed at a specified angle to the skin but still in direct contact, with gel used to maintain an acoustic path. Alternatively the transducers may be placed some distance above the skin with a coupling medium or media, which may be solids or fluids, placed between the transducer and the skin. The transducers may be angled or kept at normal incidence. By placing the transducers at an angle to the bone surface (with holders 43), particular guided wave modes may be preferentially excited and measured. The angle may be varied during a measurement Alternatively, an array of transducers may be employed, where each transducer element can function either as a transmitter or a receiver. With such an array, the received signal may be obtained as a function of transmitter-receiver distance without any mechanical scanning. In addition, under electronic control such an array may be used for beam forming and beam steering, allowing the angle of the "transmitter" and "receiver" to the bone surface to be varied.

Figure 11:
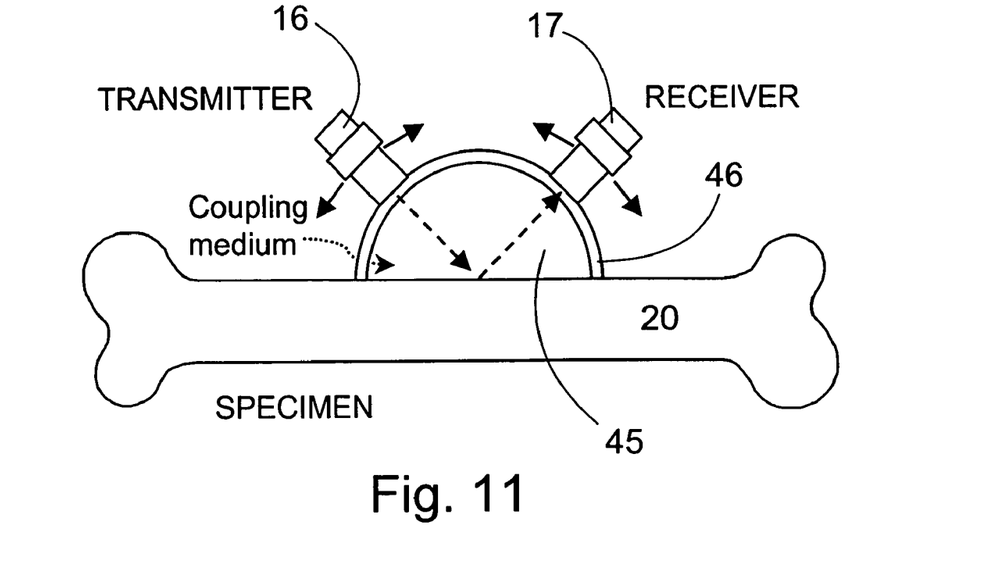
FIG. 11. Schematic diagram of the guided wave reflection measurement system for a preferred embodiment of the invention.

FIG. 11 shows schematically a another embodiment of the invention in which guided waves are measured with two transducers 16, 17 using a reflection approach. A container 46 contains liquid as coupling medium 45. Transmitter and receiver are configured so that the angle of incidence is equal to the angle of reflection. The transmitter emits an ultrasonic signal, which may be a pulse, toneburst or continuous waves, and the signal reflected from the bone surface is detected by the receiver. At a given angle, the received signal is a function of frequency with minima at frequencies corresponding to instances where energy is coupled into a guided wave mode in the bone layer. The angle of incidence ($\theta$) can be related to the phase velocity (c) of guided waves in the bone using Snell's Law, as follows, $$c = c_1 / \sin \theta$$

where $c_1$ is the velocity of sound in the coupling medium. Hence by acquiring data over a range of angles, it is possible to detect guided waves and to characterise them in terms of phase velocity and frequency. Dispersion curves similar to those in FIG. 5 can be produced.

Figure 12:
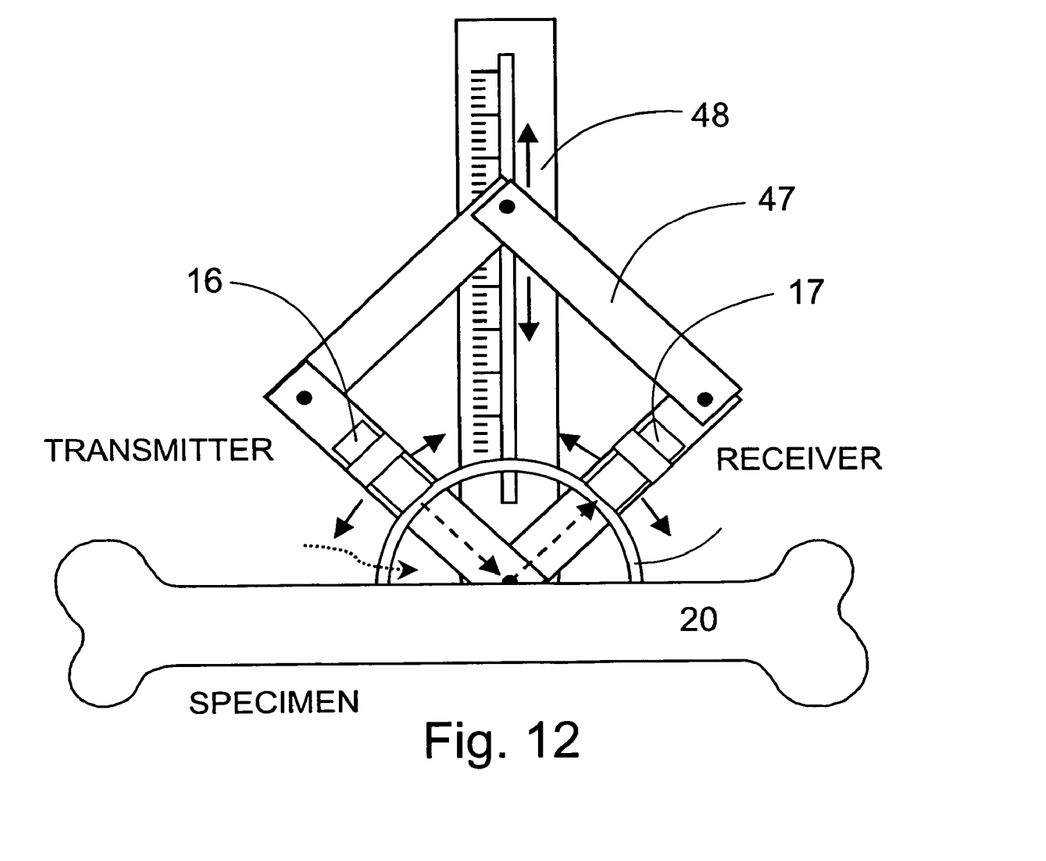
FIG. 12. Mechanism for transducer movement for purposes of reflection measurements.

FIG. 12 shows an embodiment for a mechanism for varying the angle and orientation of a pair of transducers 16, 17 whilst ensuring that the angle of incidence is equal to the angle of reflection at all times and that the transducer beam axes coincide at a point. This point should correspond with the position of the bone surface. The vertical position of the transducers may be varied to find the bone surface. A parallelogram 47 has four pieces jointed together and the upper joint moves along a vertical guide 48. The transducers 16, 17 are secured onto the lower pieces.

Figure 13:
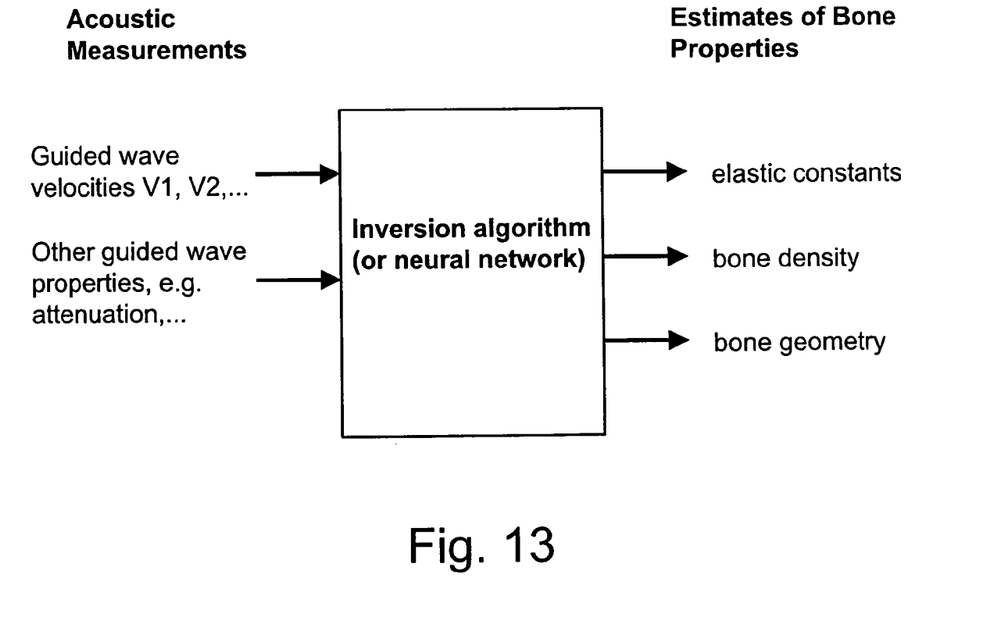
FIG. 13. Schematic diagram of the estimation of bone properties from measured acoustic parameters in a preferred embodiment of the invention.

FIG. 13 shows schematically how the acoustic measurements may be used as input data to a mathematical algorithm for estimating specific bone properties of interest.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

The invention claimed is:

1. A method for non-invasive assessment of bones, the method comprising the steps of:
   providing at least one transducer that functions as a transmitter and at least one transducer that functions as a receiver;
   directing in vivo an ultrasound signal emitted by the transmitter onto a bone, the ultrasound signal propagating within the bone and being emitted from the bone,
   detecting in vivo the ultrasound signal emitted from the bone with the receiver at two or more transmitter-to-receiver distances along the bone and recording the detected ultrasound signal,
   calculating at least one bone property from the recorded signals using a method including
      detecting one or more modes of Lamb waves, said one or more detected wave modes having a relationship with said bone property or properties,
      measuring the velocity of said one or more detected wave modes, and
      calculating the bone property or properties from the measured velocity or velocities.

2. Method according to claim 1, wherein the detected Lamb wave mode is the lowest asymmetric mode (the A0 mode).

3. Method according to claim 2, including
   detecting two wave modes and measuring and recording velocities of the two wave modes, one mode being said A0 mode and the other mode being a first arriving wave,
   producing an image of the amplitude of the received signal as a function of time and transmitter-to-receiver distance from the recorded signals,
   identifying at least two propagating waves from the image, and
   determining velocities of said propagating waves from the slopes of lines fitted to the propagating waves in the image.

4. Method according to claim 3, including
   measuring the arriving signal at least at two different transmitter-to-receiver distances,
   scanning the bone for a chosen length by sending signals in at one transmitting point and receiving response signals at a separate receiving point,
   during the measurement, moving either the transmitting or receiving point, or both, continuously or in steps, and
   recording the received response signals from a number of differing transmitter-to-receiver distances during the scan.

5. Method according to claim 3 wherein the contact pressure of the transducers are controlled by detecting the axial force and moving the transducers respectively.

6. Method according to claim 3 wherein the transmitting and/or the receiving transducer are placed at an angle to the bone surface and the ultrasonic beam travels to and from the bone through an intervening coupling medium.

7. Method according to claim 3 wherein the angle of the transducers to the bone can be changed during the measurement to identify particular angles favorable to the production and detection of specific types of waves.

8. Method according to claim 3 wherein the transmitting and/or receiving transducers are arrays of individual transducers that may be electronically controlled to achieve scanning without mechanical movement and/or to enhance the production and detection of specific waves, for example through electronically forming and steering the acoustic beam.

9. Method according to claim 3 wherein a Fourier transform is performed on the received signals to facilitate discrimination and measurement of one or more waves.

10. Method according to claim 3 wherein time-frequency analysis is performed on the received signals to facilitate discrimination and measurement of one or more waves.

11. Method according to claim 3 wherein a 2-dimensional Fourier transform is performed on the received signals as function of time and transmitter-to-receiver distance to facilitate discrimination and measurement of one or more waves.

12. Method according to claim 3 wherein filtering of the received signals is performed to facilitate discrimination and measurement of one or more waves.

13. Method according to claim 3 wherein a specified excitation signal is sent to the transmitting transducer in order to modify the frequency spectrum of the emitted signal and hence facilitate discrimination and measurement of one or more waves.

14. Method according to claim 3 wherein the phase velocity of a wave is determined by fitting a line to points of constant phase within a wave packet.

15. Method according to claim 3 wherein the group velocity of a wave is determined by fitting a line to the amplitude envelope of a wavepacket.

16. Method according to claim 1 wherein transmitting and/or receiving transducers are comb transducers composed of several transducer elements spaced a constant distance apart, so that they excite and detect guided waves with a constant wavelength determined by the spacing of the elements.

17. Method according to claim 1 wherein the attenuation of a wave is determined from a decrease in amplitude of that wave with increasing transmitter-to-receiver distance.

18. Method according to claim 1 wherein a low frequency of ultrasound is used such that the first arriving signal detected corresponds to the fundamental symmetric Lamb wave (S0 wave) in the bone.

19. Method according to claim 1 wherein a single transducer is aligned at right angles to the bone surface and is operated in pulse-echo mode, transmitting an ultrasonic signal to the bone and detecting the reflected signal from the bone and the time difference between the reflection from the upper and lower bone surfaces is determined, and is used to estimate bone thickness.

20. Method according to claim 1 wherein bone properties are estimated from Lamb wave measurements using a mathematical algorithm, comprising:

the calculation of Lamb wave parameters from a set of assumed bone properties using analytical Lamb wave theory, comparison of the calculated Lamb wave parameters with the measured Lamb wave parameters, and derivation of an error parameter representing the difference between the two, adjustment of the initial estimates of bone properties in such a way as to reduce the error parameter, and repeated iteration of this process until the error parameter becomes acceptably small, the values of the bone properties then being taken as the best estimates of the true bone properties.

21. Method according to claim 1 wherein bone properties are estimated from Lamb wave measurements using an artificial neural network, comprising:
   use of the measured Lamb wave parameters as input data for an artificial neural network whose outputs correspond to selected bone properties, and
   training of said artificial neural network with experimental data from a range of bone phantoms and real bone samples of varying physical properties.

22. Method according to claim 1 wherein measurements are made at a number of locations within a bone so as to identify and characterize regions of abnormal bone properties.

* * * * *